US012588962B2

(12) United States Patent
Hashimoto

(10) Patent No.: US 12,588,962 B2
(45) Date of Patent: Mar. 31, 2026

(54) MEDICAL SUPPORT ROBOT AND MEDICAL ROBOT SYSTEM

(71) Applicant: KAWASAKI JUKOGYO KABUSHIKI KAISHA, Kobe (JP)

(72) Inventor: Yasuhiko Hashimoto, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 349 days.

(21) Appl. No.: 17/995,711

(22) PCT Filed: Apr. 8, 2021

(86) PCT No.: PCT/JP2021/014946
§ 371 (c)(1),
(2) Date: Oct. 7, 2022

(87) PCT Pub. No.: WO2021/206152
PCT Pub. Date: Oct. 14, 2021

(65) Prior Publication Data
US 2023/0134949 A1 May 4, 2023

(30) Foreign Application Priority Data
Apr. 10, 2020 (JP) ................................ 2020-071344

(51) Int. Cl.
| | |
|---|---|
| *A61B 34/35* | (2016.01) |
| *A61B 90/00* | (2016.01) |
| *A61B 90/70* | (2016.01) |
| *B25J 5/00* | (2006.01) |
| *A61G 12/00* | (2006.01) |

(52) U.S. Cl.
CPC .............. *A61B 34/35* (2016.02); *A61B 90/37* (2016.02); *A61B 90/70* (2016.02); *B25J 5/00* (2013.01); *A61G 12/001* (2013.01)

(58) Field of Classification Search
CPC ......... A61B 34/35; A61B 34/32; A61B 90/37; A61B 90/70; A61B 90/50; A61B 50/13; A61B 2090/0813; A61B 2090/371; A61B 2034/256; B25J 5/00; B25J 5/007; B25J 5/008; B25J 15/0491; B25J 19/0058;
(Continued)

(56) References Cited

U.S. PATENT DOCUMENTS

| | | | |
|---|---|---|---|
| 2009/0234444 A1 | 9/2009 | Maschke | |
| 2012/0029697 A1* | 2/2012 | Ota | A61G 7/08 |
| | | | 348/148 |

(Continued)

FOREIGN PATENT DOCUMENTS

| | | |
|---|---|---|
| CN | 106822957 A | 6/2017 |
| DE | 102010021037 A1 | 11/2011 |

(Continued)

*Primary Examiner* — Nhi Q Bui
(74) *Attorney, Agent, or Firm* — METROLEX IP LAW GROUP, PLLC; Robert L. Scott, Esq.

(57) ABSTRACT

A medical support robot includes: a storage that houses a medical instrument; at least one robotic arm including a tip including an end effector that handles the medical instrument; a traveling structure that supports the storage and the at least one robotic arm and travels; and circuitry that performs control that may comprising causing the traveling structure to move to a medical robot that is a robot that performs medical practice.

13 Claims, 5 Drawing Sheets

(58) Field of Classification Search
CPC . A61G 12/001; A61L 2/16; A61L 2/22; A61L 2202/14; A61L 2202/15; A61L 2202/16
See application file for complete search history.

(56) References Cited

U.S. PATENT DOCUMENTS

| | | | |
|---|---|---|---|
| 2016/0132059 A1* | 5/2016 | Mason ................. | B65G 1/1373 |
| | | | 701/28 |
| 2016/0271803 A1* | 9/2016 | Stewart ............... | B25J 11/0085 |
| 2017/0322718 A1* | 11/2017 | Ballantyne ............ | H04N 7/142 |
| 2020/0100846 A1* | 4/2020 | Huang ................. | A61B 6/4458 |
| 2020/0315738 A1* | 10/2020 | Dewaele ............... | A61B 34/71 |
| 2021/0153958 A1* | 5/2021 | Meglan ................ | G05D 1/0274 |
| 2021/0338351 A1 | 11/2021 | Blondel et al. | |
| 2021/0369080 A1 | 12/2021 | Takahashi et al. | |

FOREIGN PATENT DOCUMENTS

| | | | |
|---|---|---|---|
| JP | 2009-213892 A | 9/2009 | |
| WO | 2019/096933 A2 | 5/2019 | |
| WO | 2019/096933 A3 | 5/2019 | |
| WO | 2019/123874 A1 | 6/2019 | |
| WO | 2020/065209 A1 | 4/2020 | |

* cited by examiner

MEDICAL SUPPORT ROBOT AND MEDICAL ROBOT SYSTEM

CROSS REFERENCE TO RELATED APPLICATION

This application claims priority to and the benefit of Japanese Patent Application No. 2020-071344 filed with the Japan Patent Office on Apr. 10, 2020, the entire disclosure of which is incorporated herein by reference.

TECHNICAL FIELD

The present disclosure relates to a medical support robot and a medical robot system.

BACKGROUND ART

In recent years, the introduction of robots into medical sites has been discussed. For example, PTL 1 discloses a robot X-ray imager. The robot X-ray imager includes a robotic arm, a support arm supported by the robotic arm, an X-ray source attached to the support arm, and a radiation detector attached to the support arm. During a medical treatment, the robot X-ray imager irradiates a region including a heart valve of a patient with X rays from projection directions different from each other by using the robotic arm, detects by the radiation detector the X rays attenuated in the different projection directions by the patient, and sends projection data sets corresponding to the projection directions. Moreover, a 3D image is generated from the projection data sets and is displayed on a display.

CITATION LIST

Patent Literature

PTL 1: Japanese Laid-Open Patent Application Publication No. 2009-213892

SUMMARY OF INVENTION

In recent years, various new infectious diseases prevail. Infected persons of such infectious diseases may spread the infectious diseases to others through infectious disease sources contained in, for example, droplets from the infected persons. Especially, medical workers who examine and treat the infected persons are at high risk of infection. Moreover, medical appliances used for treating the infected persons are contaminated by the infectious disease sources. Therefore, persons who supports medical practice, for example, who handles the medical appliances after the treatment are also at high risk of infection.

An object of the present disclosure is to provide a medical support robot and a medical robot system, each of which can perform work of supporting medical practice.

A medical support robot according to one aspect of the present disclosure includes: a storage that houses a medical instrument; at least one robotic arm including a tip including an end effector that handles the medical instrument; a traveling structure that supports the storage and the at least one robotic arm and travels; and a controller. The controller performs control of causing the traveling structure to move to a medical robot that is a robot that performs medical practice.

The above objects, features and advantages of the present disclosure and other objects, features and advantages of the present disclosure will be made clear by the following detailed explanation of preferred embodiments with reference to the accompanying drawings.

DESCRIPTION OF EMBODIMENTS

Hereinafter, embodiments of the present disclosure will be described with reference to the drawings. The embodiments described below are comprehensive or specific examples. Among components in the following embodiments, components that are not recited in independent claims which embody the broadest concept of the present disclosure will be described as optional components. The diagrams in the accompanying drawings are schematic diagrams and are not necessarily strictly drawn. In the diagrams, the same reference signs are used for the substantially identical components, and the repetition of the same explanation may be avoided, or such explanation may be simplified.

Configuration of Medical Robot System

Figure 1:
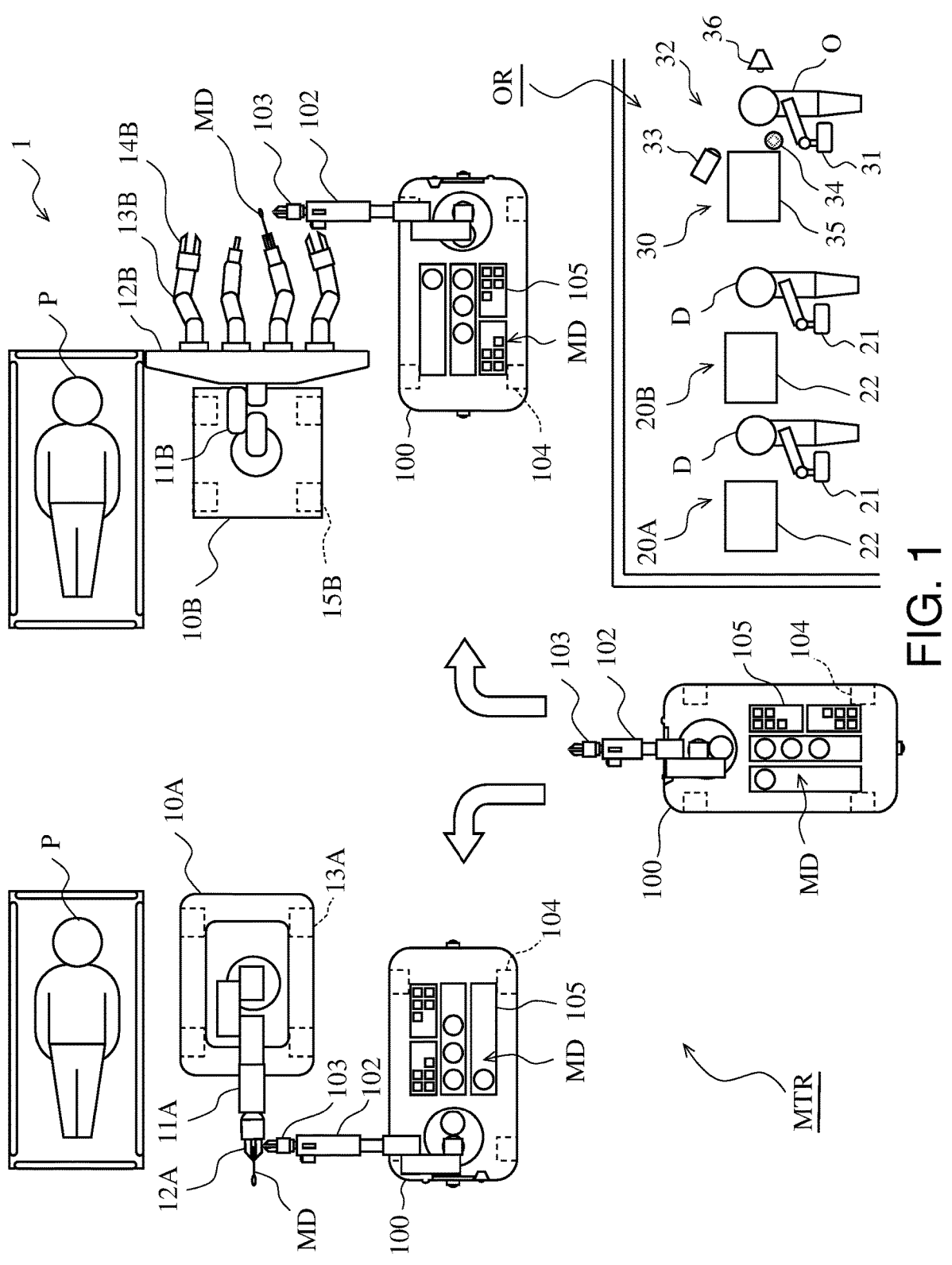
FIG. 1 is a plan view showing one example of the configuration of a medical robot system according to an embodiment.

FIG. 1 is a plan view showing one example of the configuration of a medical robot system 1 according to an embodiment. As shown in FIG. 1, the medical robot system 1 is a system that performs medical practice by using robots. The medical robot system 1 includes a medical robot 10, a medical support robot 100, and manipulation inputters 20 and 30. The medical robot 10 is a robot that performs the medical practice for a medical practice target person P, such as a to-be-examined person, a to-be-inspected person, or a patient, and FIG. 1 shows medical robots 10A and 10B. The medical support robot 100 is a robot that supports the medical practice of the medical robots 10A and 10B. The manipulation inputter 20 is a device that manipulates the medical robot 10A or 10B. FIG. 1 shows a manipulation inputter 20A for the medical robot 10A and a manipulation inputter for the medical robot 10B. The manipulation inputter 30 is a device that manipulates the medical support robot 100. The medical practice may be any practice for the treatment of the medical practice target person. Examples of the medical practice includes examination, diagnosis, inspection, care, treatment, medical operation, and surgical operation.

Hereinafter, the "medical robot 10A" and the "medical robot 10B" will be described when the medical robots 10A and 10B are distinguished from each other, and the "medical robot 10" will be described when the medical robots 10A and 10B are not distinguished from each other. The "manipulation inputter 20A" and the "manipulation inputter 20B" will be described when the manipulation inputters 20A and 20B are distinguished from each other, and the "manipulation inputter 20" will be described when the manipulation inputters 20A and 20B are not distinguished from each other.

In the present embodiment, the medical robot 10A is a newly developed robot that utilizes a general purpose robot, such as a movable industrial robot, is based on the general purpose robot, and has been devised by the inventors of the technique of the present disclosure. However, the present embodiment is not limited to this. The medical robot 10A includes: a robotic arm 11A; an end effector 12A at a tip of the robotic arm 11A; a traveling structure 13A that supports the robotic arm 11A and causes the robotic arm 11A to travel; and an interface. The medical robot 10A may be supplied with electric power from an external commercial power supply, may include a storage battery as an electric power source, or may have both of these configurations.

The end effector 12A has a structure suitable for the medical practice and is attachable to and detachable from the tip of the robotic arm 11A. For example, the end effector 12A may have a structure that accommodates to perform various medical practice, such as inspection practice, specimen collection, temperature measurement, attachment and detachment of medical appliances to and from the medical practice target person, connection and disconnection between the medical appliances attached to the medical practice target person, holding, and suction. The robotic arm 11A is an articulated robotic arm with multiple degrees of freedom. The traveling structure 13A may move the robotic arm 11A and, for example, includes wheels. For example, the traveling structure 13A may be an AGV (Automated Guided Vehicle). The interface includes a camera, a microphone, a monitor, a speaker, and the like. The camera and the microphone acquire images and sounds (including sound and voice) of, for example, the medical practice target person P and transmit them to the manipulation inputter 20A. The monitor and the speaker receive images and sounds (including sound and voice) of, for example, a doctor D as an operator from the manipulation inputter 20A and output them.

In the present embodiment, the medical robot 10B is a newly developed robot that utilizes a surgical robot, is based on the surgical robot, and has been devised by the inventors of the technique of the present disclosure. However, the present embodiment is not limited to this. The medical robot 10B includes: an arm 11B; a base 12B at a tip of the arm 11B; manipulators 13B supported by the base 12B; end effectors 14B; a traveling structure 15B; and an interface. Instead of surgical appliances, the medical robot 10B includes the end effectors 14B at the tips of the manipulators 13B. The medical robot 10B may be supplied with electric power from an external commercial power supply, may include a storage battery as an electric power source, or may have both of these configurations.

As with the end effector 12A of the medical robot 10A, the end effector 14B has a structure suitable for the medical practice and is attachable to and detachable from the tip of the manipulator 13B. The traveling structure 15B may move the medical robot 10B and, for example, may be a traveling structure included in a surgical robot. The interface includes a camera, a microphone, a monitor, a speaker, and the like. The camera and the microphone acquire images and sounds of, for example, the medical practice target person P and transmit them to the manipulation inputter 20B. The monitor and the speaker receive images and sounds of, for example, the doctor D from the manipulation inputter 20B and output them.

For example, the medical robots 10A and 10B are in a medical treatment room MTR where the medical treatment is performed for the medical practice target person P. The medical robots 10A and 10B communicate with the manipulation inputters 20A and 20B in a manipulation room OR located outside the medical treatment room MTR. The medical treatment room MTR and the manipulation room OR are isolated from each other such that, for example, pathogens, such as infectious disease sources, cannot move therebetween. The medical robot 10A transmits and receives information, commands, data, and the like to and from the manipulation inputter 20A and operates in accordance with the information, the commands, and the like received from the manipulation inputter 20A. The medical robot 10B transmits and receives information, commands, data, and the like to and from the manipulation inputter 20B and operates in accordance with the information, the commands, and the like received from the manipulation inputter 20B. To be specific, the medical robots 10A and 10B are remotely manipulated by the manipulation inputters 20A and 20B located in a space that is isolated from the medical robots 10A and 10B.

For example, as the manipulation inputter 20A for the medical robot 10A, a device similar to a manipulation inputter used for an industrial robot may be used, or a new or novel manipulation inputter devised for the medical robot 10A may be used. As the manipulation inputter 20B for the medical robot 10B, a device similar to a manipulation inputter used for a surgical robot, such as a console, may be used. Communication between the medical robots 10A and 10B and the manipulation inputters 20A and 20B may include any type of wired communication and any type of wireless communication.

Each of the manipulation inputters 20A and 20B includes an inputter 21 and an interface 22. The inputter 21 receives inputs from the doctor D who is the operator. The interface 22 includes a camera, a microphone, a monitor, a speaker, and the like. The camera and the microphone acquire images and sounds of, for example, the doctor D and transmit them to the medical robot 10A or 10B. The monitor and the speaker receive images and sounds of, for example, the medical practice target person P from the medical robot 10A or 10B and output them. Therefore, the doctor D in the manipulation room OR isolated from the medical practice target person P can perform the medical practice by using the medical robot 10A or 10B while communicating with the medical practice target person P.

Configuration of Medical Support Robot

Figure 2:
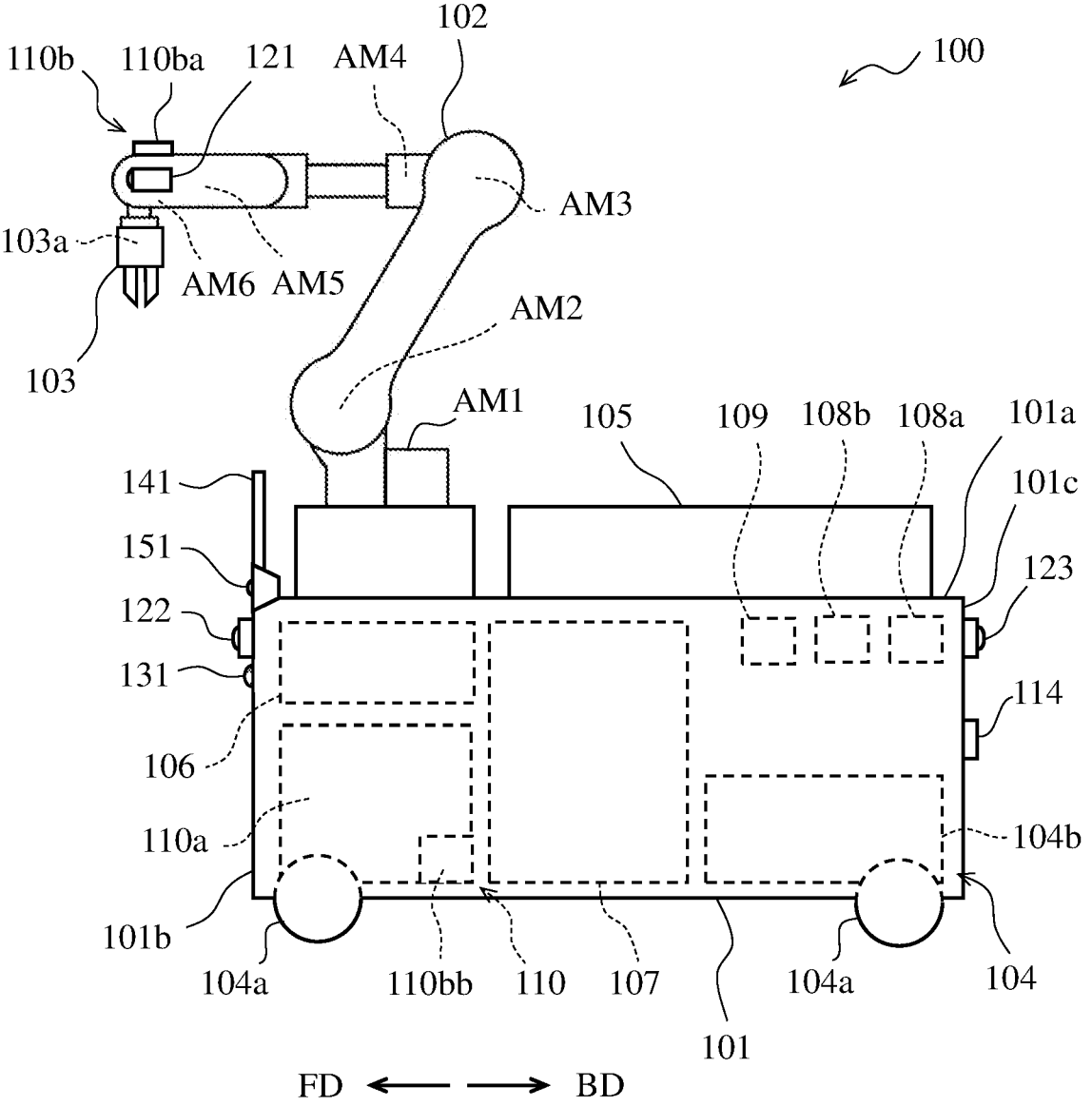
FIG. 2 is a side view showing one example of the configuration of a medical support robot according to the embodiment.
Figure 3:
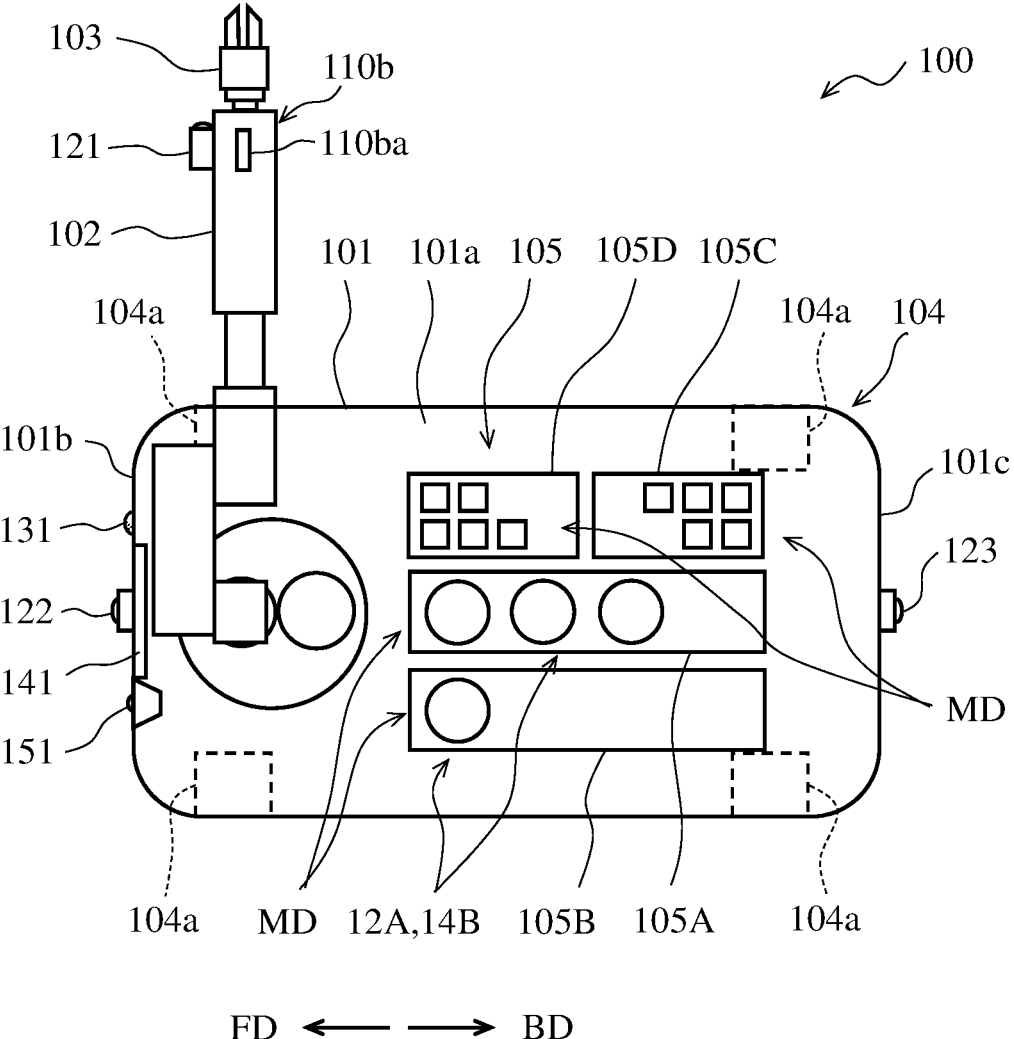
FIG. 3 is a plan view showing one example of the configuration of the medical support robot according to the embodiment.

The configuration of the medical support robot 100 will be described. FIG. 2 is a side view showing one example of the configuration of the medical support robot 100 according to the embodiment. FIG. 3 is a plan view showing one example of the configuration of the medical support robot 100 according to the embodiment. As shown in FIGS. 2 and 3, the medical support robot 100 includes a base 101, a robotic arm 102, an end effector 103, a traveling structure 104, a storage 105, and a controller 106. The robotic arm 102 and the storage 105 are located on an upper surface 101a of the base 101 and are supported by the base 101. The end effector 103 is detachably attached to a tip of the robotic arm 102 and has a structure suitable for a medical support operation. The traveling structure 104 is located at a lower portion of the base 101 and moves the base 101. To be specific, the traveling structure 104 supports the robotic arm 102 and the storage 105 and can travel. The controller 106 controls operations of the robotic arm 102, the end effector 103, the traveling structure 104, and the like.

The robotic arm 102 can freely change the position and posture of the end effector 103 at the tip of the robotic arm 102. The robotic arm 102 is a robotic arm with multiple degrees of freedom and includes joints. In the present embodiment, the robotic arm 102 is a six-axis vertically articulated robotic arm including six rotary joints. However, the type of the robotic arm 102 is not limited to this. The robotic arm 102 includes arm drivers AM1 to AM6 that respectively rotate the six joints. The arm drivers AM1 to AM6 use electric power as a power source and, for example, include servomotors as electric motors. The operations of the arm drivers AM1 to AM6 are controlled by the controller 106.

The end effector 103 can handle a medical instrument MD. A power source of a tool driver 103a that is a driver of the end effector 103 is not especially limited but may be, for example, electric power, pneumatic pressure, liquid pressure, or the like. The tool driver 103a that uses electric power as the power source includes, for example, a servomotor as an electric motor. The operation of the tool driver 103a is controlled by the controller 106.

The medical instrument MD may be any device used for medical care. Examples of the medical instrument MD may include medical appliances, medical tools, inspection appliances, inspection tools, specimens, medicines, carrying structures on which the medical practice target persons rest, and the end effectors 12A and 14B of the medical robots 10A and 10B. However, the present embodiment is not limited to these. For example, the medicines includes not only medicines but also articles, such as blood for transfusion and culture liquid, which are introduced into the bodies of the medical practice target persons. Examples of the carrying structures may include beds, examination tables, operating tables, stretchers, and wheelchairs. However, the present embodiment is not limited to these.

The storage 105 can house the medical instruments MD. In the present embodiment, the storage 105 includes storages 105A to 105D. However, the present embodiment is not limited to this. The first storage 105A houses the end effectors 12A and 14B which have not been used for the treatment of the medical practice target person or have been disinfected. For example, the first storage 105A houses the end effectors 12A and 14B which may be used by the medical robots 10A and 10B for various treatments. The second storage 105B houses the end effectors 12A and 14B which have already been used for the treatment of the medical practice target person. For example, the second storage 105B houses the end effectors 12A and 14B which have been detached from the medical robots 10A and 10B.

The third storage 105C houses the medical instruments MD which have not been used for the treatment of the medical practice target person among the medical instruments MD handled by the end effectors 12A and 14B of the medical robots 10A and 10B. For example, the third storage 105C may house medical appliances, medical tools, inspection appliances, inspection tools, specimens, medicines, and the like. For example, the third storage 105C may house inspection tools, inspection kits, and the like which are used to collect specimens from the medical practice target persons.

The fourth storage 105D houses the medical instruments MD which have already been used for the treatment of the medical practice target person among the medical instruments MD handled by the end effectors 12A and 14B. For example, the fourth storage 105D may house medical appliances, medical tools, inspection appliances, inspection tools, specimens, medicines, and the like. For example, the fourth storage 105D may house inspection tools, inspection kits, and the like which have been used to collect specimens from the medical practice target persons.

The end effector 103 can hold the medical instrument MD in the storage 105, take out the medical instrument MD from the storage 105, and put the medical instrument MD into the storage 105. Furthermore, the end effector 103 can perform at least either one of a holding operation of causing the medical robot 10A or 10B to hold the medical instrument MD which has been taken out from the storage 105 or a hold releasing operation of causing the medical robot 10A or 10B to release the medical instrument MD held by the medical robot 10A or 10B.

Specifically, the end effector 103 may be able to attach the end effector 12A to the robotic arm 11A and attach the end effector 14B to the manipulator 13B. The end effector 103 may be able to detach the end effector 12A attached to the robotic arm 11A and detach the end effector 14B attached to the manipulator 13B. The end effector 103 may be able to attach or hand over the medical instrument MD other than the end effectors 12A and 14B to the end effector 12A or 14B. The end effector 103 may be able to detach or receive the medical instrument MD, held by the end effector 12A or 14B, from the end effector 12A or 14B.

The traveling structure 104 includes wheels 104a and a traveling driver 104b. The wheels 104a can support and move the base 101. The traveling driver 104b can drive at least one of the wheels 104a and turn at least one of the wheels 104a. With this, the traveling driver 104b can move the base 101 in any direction. The traveling structure 104 may be able to move the base 101 by using power. In the present embodiment, the traveling driver 104b uses electric power as a power source and, for example, includes a servomotor as an electric motor. However, the present embodiment is not limited to this. For example, the traveling structure 104 may be an AGV. The operation of the traveling driver 104b is controlled by the controller 106.

The medical support robot 100 includes a storage battery 107, a communicator 108, a position detector 109, and a disinfectant storage 110a of a disinfector 110 in the base 101. The storage battery 107 serves as an electric power source of electrical structures of the medical support robot 100. The storage battery 107 is a secondary battery that can be charged or discharged. Examples of the secondary battery includes lead storage batteries, lithium ion secondary batteries, nickel-hydrogen storage batteries, and nickel-cadmium storage batteries. The storage battery 107 is electrically connected to a power supply connector 114 located at the base 101. The storage battery 107 is supplied with electric power from, for example, an external commercial power supply connected to the power supply connector 114, stores the supplied electric power, and supplies the stored electric power to the electrical structures of the medical support robot 100. The medical support robot 100 may supply electric power, supplied from, for example, an external commercial power supply connected to the power supply connector 114, to the electrical structures of the medical support robot 100 or may selectively use the electric power of the storage battery 107 or the electric power of, for example, the commercial power supply or use both the electric power of the storage battery 107 and the electric power of, for example, the commercial power supply.

The communicator 108 includes a first communicator 108a and a second communicator 108b. The first communicator 108a communicates with the manipulation inputter 30 of the medical support robot 100 through wireless communication or wired communication. The transmission and reception of information, commands, data, and the like between the controller 106 and the manipulation inputter 30 are performed through the first communicator 108*a*. The second communicator 108*b* communicates with the medical robots 10A and 10B through wireless communication or wired communication. The transmission and reception of information, commands, data, and the like between the controller 106 and the medical robots 10A and 10B are performed through the second communicator 108*b*. In the present embodiment, the communicators 108*a* and 108*b* perform wireless communication. However, the present embodiment is not limited to this. Each of the communicators 108*a* and 108*b* may include, for example, communication circuitry. The wireless communication and the wired communication applied to the communicators 108*a* and 108*b* may be any type of wireless communication and any type of wired communication. Only the first communicator 108*a* may be included among the communicators 108*a* and 108*b*.

For example, the medical support robot 100 is located in the medical treatment room MTR as with the medical robots 10A and 10B, and the manipulation inputter 30 is located in the manipulation room OR as with the manipulation inputters 20A and 20B for the medical robots 10A and 10B. Therefore, the medical support robot 100 is remotely manipulated by the manipulation inputter 30 located in a space isolated from the medical robots 10A and 10B and the medical support robot 100.

The position detector 109 may detect the position of the base 101 and further detect the posture of the base 101. The position detector 109 outputs a detection result to the controller 106. The configuration of the position detector 109 is not especially limited. The position detector 109 may detect at least the position of the base 101 among the position and posture of the base 101.

For example, the position detector 109 may include a position measurer, such as a GPS (Global Positioning System) receiver or an IMU (Inertial Measurement Unit). The position detector 109 may detect the position and posture of the base 101 by using, for example, received signals of the GPS receiver and/or acceleration, angular velocity, and the like measured by the IMU. For example, the position detector 109 may detect the position and posture of the base 101 based on signals received from a sensor located around the position detector 109. For example, the position detector 109 may detect the position and posture of the base 101 by emitting infrared light, light wave, ultrasound, or the like to its periphery and receiving a reflected wave of the infrared light, the light wave, the ultrasound, or the like. For example, the position detector 109 may detect the position and posture of the base 101 based on an image of the periphery taken by the camera. For example, the position detector 109 may detect weak induction current from an electric wire embedded in a floor surface and detect the position and posture of the base 101 based on a detected value of the induction current.

The disinfector 110 includes the disinfectant storage 110*a* and an ejector 110*b*. The disinfectant storage 110*a* is a container that houses disinfectant. For example, the disinfectant storage 110*a* houses disinfectant solution, such as alcohol. The ejector 110*b* is connected to the disinfectant storage 110*a* through piping or the like and ejects the disinfectant of the disinfectant storage 110*a* to an outside. For example, the ejector 110*b* may be a device that ejects disinfectant solution or disinfectant powder. Then, the ejector 110*b* includes an ejection nozzle 110*ba* and a pump 110*bb* that pumps the disinfectant. The ejection nozzle 110*ba* is located at the robotic arm 102 or the end effector

103 and can eject the disinfectant in an arbitrary direction at an arbitrary position by the operations of the robotic arm 102 and the end effector 103. In the present embodiment, the ejection nozzle 110*ba* is located at the tip of the robotic arm 102. The pump 110*bb* is located in the base 101.

The medical support robot 100 includes at least one imager 121, 122, 123, a sound inputter 131, a display 141, and a sound outputter 151. In the present embodiment, three imagers 121 to 123 are included. However, the present embodiment is not limited to this. The first imager 121 is located at the tip of the robotic arm 102. However, the first imager 121 may be located at the end effector 103 or another portion of the robotic arm 102. The first imager 121 can be located at an arbitrary position and an arbitrary orientation by the robotic arm 102. For example, the first imager 121 takes an image of a target to which the end effector 103 applies an action, and outputs image data as one example of the image signals to, for example, the controller 106. The first imager 121 is a camera that takes a digital still image and/or a digital video and may be a 3D camera that can take a 3D image including the positional information of a subject in the image.

The second imager 122 is located on a side surface 101*b* of the base 101. The side surface 101*b* is a side surface located in a front direction FD that is an advancing direction of the base 101 that advances by the traveling structure 104. The robotic arm 102 is located in the vicinity of the side surface 101*b*. For example, the second imager 122 is a wide angle camera that takes a digital still image and/or a digital video. The second imager 122 may take an image of a wide range in the front direction FD from the side surface 101*b* and a radiation direction with respect to the front direction FD. The second imager 122 outputs taken image data to the controller 106.

The third imager 123 is located on a side surface 101*c* of the base 101. The side surface 101*c* is a side surface located in a rear direction BD that is a retreating direction of the base 101 that retreats by the traveling structure 104. The storage 105 is located in the vicinity of the side surface 101*c*. For example, the third imager 123 is a wide angle camera as with the second imager 122 and may take an image of a wide range in the rear direction BD from the side surface 101*c* and a radiation direction with respect to the rear direction BD. The third imager 123 outputs taken image data to the controller 106.

Not all the imagers 121 to 123 are essential. For example, the first imager 121 that can change its position and its orientation may be used instead of at least either one of the imager 122 or the imager 123.

The sound inputter 131 is located on the side surface 101*b* of the base 101. The sound inputter 131 receives an input of sounds, converts the sounds into sound signals, and outputs the sound signals to the controller 106. The sound inputter 131 may be any device that can receive the input of the sounds and convert the sounds into the sound signals. For example, the sound inputter 131 is a microphone. For example, the sound inputter 131 can acquire sound signals of, for example, the medical practice target person.

The display 141 is a device that outputs an image. For example, the display 141 is a liquid crystal display, an organic or inorganic EL display (Electro-Luminescence Display), or the like. However, the present embodiment is not limited to these. For example, the display 141 can display, as an image, image data of, for example, the operator taken by an imager 33 (see FIG. 1) located at the manipulation inputter 30.

The sound outputter 151 is a device that outputs sounds. The sound outputter 151 converts the sound signals into sounds and outputs the sounds. The sound outputter 151 may be any device that can convert the sound signals into the sounds. For example, the sound outputter 51 is a speaker. For example, the sound outputter 151 can convert the sound signals of the operator, output from a sound inputter 34 (see FIG. 1) located at the manipulation inputter 30, into sounds and output the sounds.

As above, the medical support robot 100 realizes the transfer of the medical instrument MD to the medical robot 10A or 10B and the communication between a person in the vicinity of the medical robot 10A or 10B and the the operator of the manipulation inputter 30. Since the medical support robot 100 does not have to perform the medical practice directly to the medical practice target person, the the operator of the manipulation inputter 30 is not limited to the medical worker.

As shown in FIG. 1, the manipulation inputter 30 includes an inputter 31 and an interface 32. The inputter 31 receives an input from an operator O. The interface 32 includes the imager 33, the sound inputter 34, a display 35, and a sound outputter 36. The imager 33, the sound inputter 34, the display 35, and the sound outputter 36 are the same in configuration as those of the medical support robot 100. The imager 33 takes an image of, for example, the operator O, and image data of the image is transmitted to the medical support robot 100 by the manipulation inputter 30. The sound inputter 34 receives the sounds of, for example, the operator O, and sound signals of the sounds is transmitted to the medical support robot 100 by the manipulation inputter 30. The display 35 displays an image corresponding to the image data received by the manipulation inputter 30 from the medical support robot 100. The sound outputter 36 outputs sounds corresponding to the sound signals received by the manipulation inputter 30 from the medical support robot 100.

The configuration of the controller 106 will be described. The controller 106 controls the operations of the components of the medical support robot 100. For example, the controller 106 includes a computer. For example, the controller 106 includes a computing unit including a processor, a memory, and the like. The computing unit transmits or receives information, data, information, commands, and the like to or from another device. The computing unit receives signals from various devices and outputs control signals to control targets. The memory includes a memory device such as a semiconductor memory (such as a volatile memory or a non-volatile memory), a hard disk or a SSD (Solid State Drive). For example, the memory stores programs executed by the computing unit, various fixed data, and the like.

The functions of the computing unit may be realized by a computer system including a processor such as a CPU (Central Processing Unit), a volatile memory such as a RAM (Random Access Memory), a non-volatile memory such as a ROM (Read-Only Memory), and the like. The computer system may realize the functions of the computing unit in such a manner that the CPU uses the RAM as a work area and executes the programs stored in the ROM. Some or all of the functions of the computing unit may be realized by the computer system, may be realized by dedicated hardware circuitry, such as an electronic circuit or an integrated circuit, or may be realized by the combination of the computer system and the hardware circuitry. The controller 106 may execute processing by centralized control performed by a single computer or may execute processing by distributed control performed by the cooperation of plural computers.

For example, the functions of the controller 106 may be realized by circuitry, such as a LSI (Large Scale Integration), a system LSI, or the like. Each of the functions of the controller 106 may be realized by a single chip, or some or all of the functions of the controller 106 may be realized by a single chip. The circuitry may be general circuitry or dedicated circuitry. As the LSI, a FPGA (Field Programmable Gate Array) that is programmable after the manufacture of the LSI, a reconfigurable processor that can reconfigure the connection and/or setting of circuit cells inside the LSI, an ASIC (Application Specific Integrated Circuit) that is a single circuit obtained by integrating plural function circuits for a specific application, or the like may be utilized.

Figure 4:
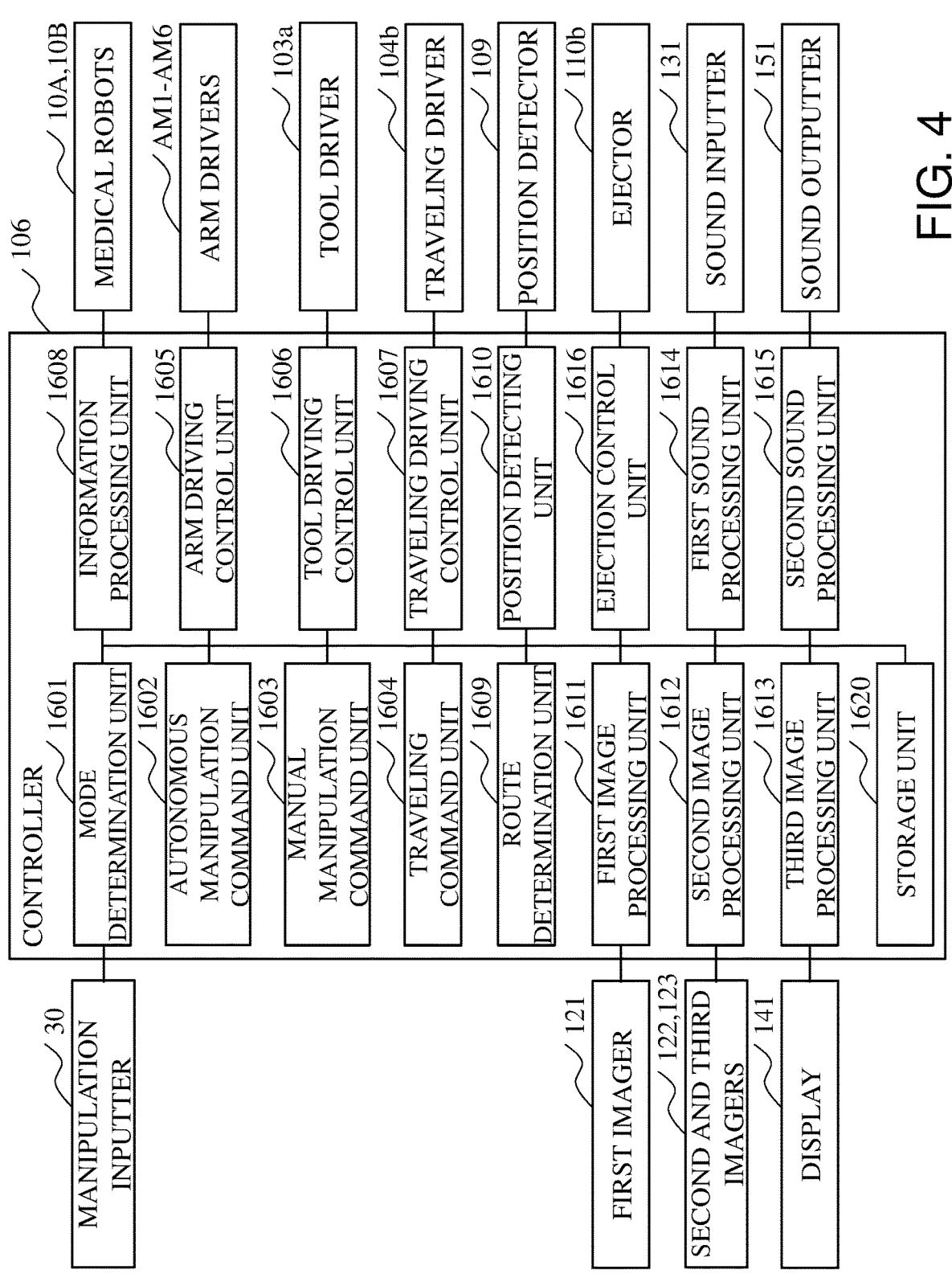
FIG. 4 is a block diagram showing one example of a functional configuration of the medical support robot according to the embodiment.

A functional configuration of the controller 106 will be described. FIG. 4 is a block diagram showing one example of the functional configuration of the medical support robot 100 according to the embodiment. As shown in FIG. 4, as functional components, the controller 106 includes a mode determination unit 1601, an autonomous manipulation command unit 1602, a manual manipulation command unit 1603, a traveling command unit 1604, an arm driving control unit 1605, a tool driving control unit 1606, a traveling driving control unit 1607, an information processing unit 1608, a route determination unit 1609, a position detecting unit 1610, a first image processing unit 1611, a second image processing unit 1612, a third image processing unit 1613, a first sound processing unit 1614, a second sound processing unit 1615, an ejection control unit 1616, and a storage unit 1620. The function of the storage unit 1620 is realized by the memory. The functions of the components other than the function of the storage unit 1620 are realized by the processor and the like. Not all the above components are essential.

The storage unit 1620 can store various information, and the stored information can be read from the storage unit 1620. For example, the storage unit 1620 may store programs, various fixed data, and the like. The storage unit 1620 stores map data of the medical treatment room MTR, map data in a structure, such as a building including the medical treatment room MTR, and the like. When there is a change in information in the map data, the storage unit 1620 may receive an update of the map data. The storage unit 1620 may store the information of the medical robots 10A and 10B which has been received by the controller 106 from the medical robots 10A and 10B. The storage unit 1620 may store the image data transmitted to the controller 106 from the imagers and the sound signals transmitted to the controller 106 from the sound outputters.

The mode determination unit 1601 determines a manipulation mode of the medical support robot 100 in accordance with a command received from the manipulation inputter 30. The manipulation mode includes: an autonomous manipulation mode in which the medical support robot 100 automatically, i.e., autonomously performs a predetermined operation in accordance with the program; and a manual manipulation mode in which the medical support robot 100 performs an operation corresponding to a manipulation command received from the manipulation inputter 30 in accordance with the manipulation command. The manipulation command is a command corresponding to manipulation input to the manipulation inputter 30 to manually manipulate the medical support robot 100.

The autonomous manipulation command unit 1602 functions in the autonomous manipulation mode. The autonomous manipulation command unit 1602 outputs to the arm driving control unit 1605 and the tool driving control unit 1606 an operation command by which the robotic arm 102 and the end effector 103 autonomously execute a predetermined operation set in the program. The operation command is a command by which the arm drivers AM1 to AM6 of the robotic arm 102 and the tool driver 103a of the end effector 103 operate.

The manual manipulation command unit 1603 functions in the manual manipulation mode. The manual manipulation command unit 1603 outputs to the arm driving control unit 1605 and the tool driving control unit 1606 an operation command by which the robotic arm 102 and the end effector 103 execute an operation corresponding to the manipulation command.

The traveling command unit 1604 outputs to the traveling driving control unit 1607 an operation command by which the traveling driver 104b of the traveling structure 104 operates. In the autonomous manipulation mode, the traveling command unit 1604 outputs an operation command by which the traveling structure 104 autonomously travels along a route set in the program. For example, the route set in the program may be a route determined by the route determination unit 1609. The traveling command unit 1604 outputs an operation command including, for example, a movement direction, orientation, speed, and acceleration of the base 101 by using the position and posture of the base 101 detected by the position detecting unit 1610 and information of the route. In the manual manipulation mode, the traveling command unit 1604 outputs an operation command by which the traveling structure 104 travels based on, for example, the movement direction, orientation, speed, and acceleration of the base 101 corresponding to the manipulation command.

The arm driving control unit 1605 controls the arm drivers AM1 to AM6 such that the arm drivers AM1 to AM6 operate in accordance with the operation commands received from the manipulation command units. The arm driving control unit 1605 controls the rotation amounts, rotational speeds, and the like of the servomotors of the arm drivers AM1 to AM6 by using the rotation amounts and the like of the servomotors of the arm drivers AM1 to AM6 as feedback information and controls the rotational torques of the servomotors of the arm drivers AM1 to AM6 by using the current values of the servomotors of the arm drivers AM1 to AM6 as feedback information.

The tool driving control unit 1606 controls the tool driver 103a such that the tool driver 103a operates in accordance with the operation commands received from the manipulation command units. The tool driving control unit 1606 controls the driving of the servomotor of the tool driver 103a by using the rotation amount, the current value, and the like of the servomotor of the tool driver 103a as feedback information.

The traveling driving control unit 1607 controls the traveling driver 104b such that the traveling driver 104b operates in accordance with the operation command received from the traveling command unit 1604. The traveling driving control unit 1607 controls the driving of the servomotor of the traveling driver 104b by using the rotation amount, the current value, and the like of the servomotor of the traveling driver 104b as feedback information.

The information processing unit 1608 processes robot information that is information of the medical robot 10A received from the medical robot 10A or information of the medical robot 10B received from the medical robot 10B, and outputs the robot information to the component corresponding to the robot information. Moreover, the information processing unit 1608 stores a part of the robot information or the whole robot information in the storage unit 1620. For example, the robot information may include: identification information of the medical robots 10A and 10B, such as IDs of the medical robots 10A and 10B; commands from the medical robots 10A and 10B; the types of the medical robots 10A and 10B, such as models of the medical robots 10A and 10B; the types of the attached end effectors 12A and 14B, such as the models of the attached end effectors 12A and 14B; and information of the medical robots 10A and 10B, such as the positions and orientations of the medical robots 10A and 10B. For example, the commands may include: commands of requests or replacements of the end effectors 12A and 14B of the medical robots 10A and 10B; commands of requests, collections, or replacements of the medical instruments MD for the end effectors 12A and 14B of the medical robots 10A and 10B; commands of conveyance of carrying structures MDA conveyed to the medical robots 10A and 10B; and commands of conveyance of the carrying structures MDA conveyed from the medical robots 10A and 10B. The information processing unit 1608 transmits a part of the robot information or the whole robot information to the manipulation inputter 30.

In the present description and the claims, each of "the information of the position" and "the positional information" may denote "only the information of the position," "the information of the position and orientation," or "the information of the position and posture."

The route determination unit 1609 functions in the autonomous manipulation mode. The route determination unit 1609 determines a route along which the medical support robot 100 moves to the medical robot 10A or 10B corresponding to the command of the robot information. The route determination unit 1609 determines the route by using the information of the position and orientation of the medical robot 10A or 10B, the information of the position and orientation of the base 101 of the medical support robot 100, and the map data of the medical treatment room MTR.

For example, as shown in FIG. 1, in some cases, the medical support robot 100 conveys the medical instrument MD housed in the storage 105 to the medical robot 10A or 10B in accordance with the command of the robot information. In this case, the route determination unit 1609 determines the route from the medical support robot 100 to the medical robot 10A or 10B.

Figure 5:
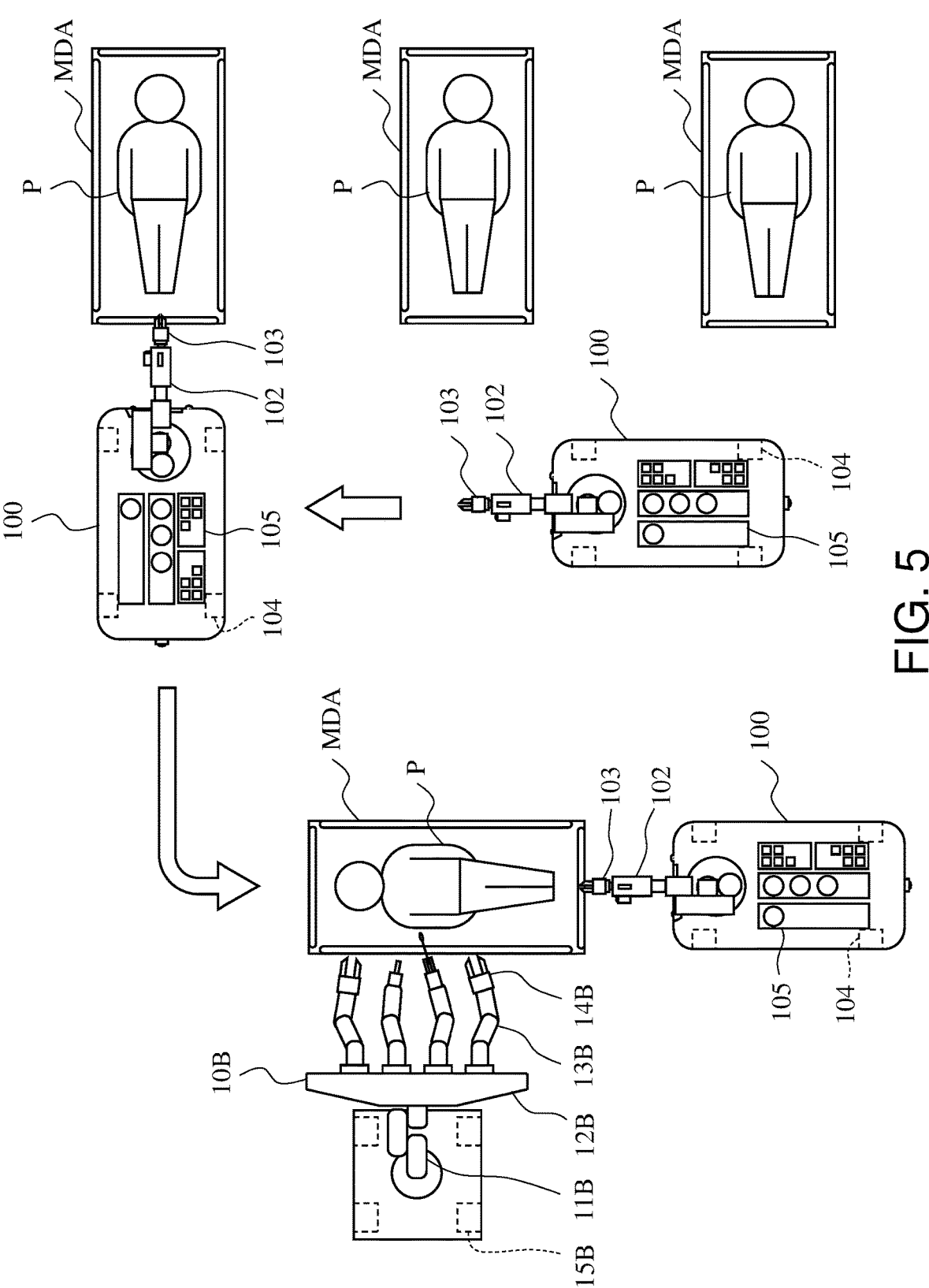
FIG. 5 is a plan view showing one example of operation of the medical support robot according to the embodiment.

For example, as shown in FIG. 5, in some cases, the medical support robot 100 conveys a bed MDA, which is one example of the carrying structure as the medical instrument MD and on which the medical practice target person P lies, to the medical robot 10A or 10B in accordance with the command of the robot information. FIG. 5 is a plan view showing one example of the operation of the medical support robot 100 according to the embodiment. In this case, the route determination unit 1609 determines the route from the medical support robot 100 through the bed MDA to the medical robot 10A or 10B. In this case, the robot information includes information, such as the identification information and positional information of the bed MDA as a conveyance target.

The position detecting unit 1610 detects the position and posture of the base 101 of the medical support robot 100 by using a detection result received from the position detector 109. The position detecting unit 1610 may transmit the information of the position and posture of the base 101 to the manipulation inputter 30. With this, the information may be used for the manipulation of the traveling structure 104 by the manipulation inputter 30.

The first image processing unit 1611 processes the image data taken by the first imager 121 of the medical support robot 100 and transmits the processed image data to the manipulation inputter 30.

The second image processing unit 1612 processes the image data taken by the second imager 122 of the medical support robot 100 and the image data taken by the third imager 123 of the medical support robot 100 and transmits the processed image data to the manipulation inputter 30. For example, the second image processing unit 1612 may perform processing, such as synthesis, such that the image data of the second imager 122 and the image data of the third imager 123 are displayed in synchronization with each other.

The third image processing unit 1613 processes the image data received from the manipulation inputter 30 and causes the display 141 to display the processed image data. For example, the third image processing unit 1613 receives the image data taken by the imager 33 of the manipulation inputter 30, processes the image data, and causes the display 141 to display the processed image data.

The first sound processing unit 1614 processes the sound signals acquired by the sound inputter 131 of the medical support robot 100 and transmits the processed sound signals to the manipulation inputter 30.

The second sound processing unit 1615 processes the sound signals received from the manipulation inputter 30 and causes the sound outputter 151 to output the processed sound signals. For example, the second sound processing unit 1615 receives the sound signals acquired by the sound inputter 34 of the manipulation inputter 30, processes the sound signals, and causes the sound outputter 151 to output the processed sound signals.

The ejection control unit 1616 controls the operation of the ejector 110*b* of the disinfector 110. For example, the ejection control unit 1616 causes the ejector 110*b* to eject the disinfectant to the robotic arm 11A of the medical robot 10A, the manipulators 13B of the medical robot 10B, and the end effectors 12A and 14B. The ejection control unit 1616 may cause the ejector 110*b* to autonomously perform the ejection in accordance with the command of the robot information or may cause the ejector 110*b* to perform the ejection in accordance with the command of the manipulation inputter 30. For example, the ejection control unit 1616 may cause the ejector 110*b* to perform the ejection at a timing of the replacement of the end effector 12A or 14B or a timing of the replacement of the medical instrument MD at the end effector 12A or 14B.

The above-described controller 106 can cause the medical support robot 100 to execute various operations of supporting the medical practice of the medical robots 10A and 10B by controlling the robotic arm 102, the end effector 103, and the traveling structure 104.

For example, the controller 106 can perform control of causing the traveling structure 104 to move to the medical robots 10A and 10B. In this case, the controller 106 can perform such control in both the autonomous manipulation mode and the manual manipulation mode.

The controller 106 can perform control of causing the robotic arm 102 and the end effector 103 to execute the holding operation of causing the medical robot 10A or 10B to hold the medical instrument MD in the storage 105 of the medical support robot 100 and the hold releasing operation of causing the medical robot 10A or 10B to release the medical instrument MD held by the medical robot 10A or

10B. For example, the replacement of the medical instrument MD can be performed. In such a case, the controller 106 can perform the control in both the autonomous manipulation mode and the manual manipulation mode. For example, the controller 106 may execute traveling control of the traveling structure 104 to the medical robot 10A or 10B in the autonomous manipulation mode and execute control of the holding operation and the hold releasing operation in the manual manipulation mode. With this, even when each of the holding operation and the hold releasing operation includes complex operation, the holding operation and the hold releasing operation can be surely executed.

For example, when performing the holding operation or the hold releasing operation, first, the controller 106 may cause the robotic arm 102 and the end effector 103 to autonomously operate such that the end effector 103 or the medical instrument MD held by the end effector 103 approaches the medical robot 10A or 10B.

Next, the controller 106 may cause the robotic arm 102 and the end effector 103 to operate in accordance with the manipulation command of the manipulation inputter 30 to execute the holding operation or the hold releasing operation by manual manipulation. In this case, the controller 106 may store in the storage unit 1620 the operation commands corresponding to the manipulation command of the manipulation inputter 30 and/or the operation information of the robotic arm 102 and the end effector 103 operated in accordance with the manipulation command.

Or, the controller 106 may cause the robotic arm 102 and the end effector 103 to operate based on the operation commands and/or the operation information stored in the storage unit 1620 to execute the holding operation or the hold releasing operation by autonomous manipulation.

Moreover, the controller 106 may learn the holding operation and the hold releasing operation. For example, while the holding operation or the hold releasing operation is executed by the autonomous manipulation, the controller 106 may receive the manipulation of the manipulation inputter 30 by the operator O and correct the ongoing operation of the robotic arm 102 and/or the end effector 103 in accordance with the inputted manipulation. In this case, the controller 106 may update the operation command and/or the operation information in the storage unit 1620 by using the operation command and/or the operation information corresponding to the corrected operation of the robotic arm 102 and/or the corrected operation of the end effector 103.

After that, when executing the holding operation or the hold releasing operation by the autonomous manipulation, the controller 106 may cause the robotic arm 102 and the end effector 103 to operate based on the updated operation command and/or the updated operation information stored in the storage unit 1620. Moreover, when the operation is corrected again using the manipulation inputter 30 by the operator O during the execution of the holding operation or the hold releasing operation, the controller 106 may update the operation command and/or the operation information in the storage unit 1620 again by using the operation command and/or the operation information corresponding to the corrected operation of the robotic arm 102 and/or the end effector 103. As above, by the repetition of the update of the operation command and/or the operation information, the operation command and/or the operation information which realize the holding operation and the hold releasing operation that are more accurate or more sophisticated are stored in the storage unit 1620. To be specific, the controller 106 can learn the holding operation and the hold releasing operation. Regarding control of the other operations of the medical support robot 100, the controller 106 may perform control similar to the above control of the holding operation and the hold releasing operation.

Moreover, the controller 106 receives the information of the specified medical robot 10A or 10B and can perform control of executing at least either one of the holding operation or the hold releasing operation based on the robot information of the medical robot 10A or 10B. To be specific, the controller 106 can execute the control in the autonomous manipulation mode.

The controller 106 can perform control of causing the end effector 103 to hold the carrying structure MDA, such as the bed on which the medical practice target person lies and causing the traveling structure 104 to move the carrying structure MDA to the medical robot 10A or 10B. In this case, the controller 106 can perform the control in both the autonomous manipulation mode and the manual manipulation mode.

For example, the controller 106 receives the information of the specified carrying structure MDA and the robot information of the specified medical robot 10A or 10B. Based on the information of the carrying structure MDA and the robot information, the controller 106 can perform control of causing the traveling structure 104 to move to the carrying structure MDA, causing the end effector 103 to hold the carrying structure MDA, and causing the traveling structure 104 to move the carrying structure MDA to the medical robot 10A or 10B.

The controller 106 can perform control of receiving the sound signals from the manipulation inputter 30 for the medical support robot 100 and causing the sound outputter 151 of the medical support robot 100 to output the sounds corresponding to the sound signals.

The controller 106 can perform control of outputting to the manipulation inputter 30 for the medical support robot 100 the sound signals corresponding to the sounds received by the sound inputter 131 of the medical support robot 100.

The controller 106 can perform control of receiving the image signals from the manipulation inputter 30 for the medical support robot 100 and causing the display 141 of the medical support robot 100 to output the image corresponding to the image signals.

The controller 106 can perform control of outputting to the manipulation inputter 30 for the medical support robot 100 the signals of the images taken by the imagers 121 to 123.

The controller 106 can perform control of outputting to the manipulation inputter 30 for the medical support robot 100 the information of the position and posture of the medical support robot 100 detected by the position detector 109 of the medical support robot 100.

Moreover, the controller 106 can perform control of causing the traveling structure 104 to autonomously move to the medical robot 10A or 10B based on the robot information of the medical robot 10A or 10B and the information of the position of posture of the medical support robot 100 detected by the position detector 109.

The controller 106 can perform control of causing the ejector 110*b* of the disinfector 110 of the medical support robot 100 to eject the disinfectant to the medical robot 10A or 10B. In this case, the controller 106 can perform the control in both the autonomous manipulation mode and the manual manipulation mode. For example, the controller 106 can perform control of causing the ejector 110*b* to autonomously eject the disinfectant to the medical robot 10A or 10B based on the robot information of the medical robot 10A or 10B.

Other Embodiments

The foregoing has described the examples of the embodiment of the present disclosure. However, the present disclosure is not limited to the above embodiment. To be specific, various modifications and improvements may be made within the scope of the present disclosure. For example, modes prepared by variously modifying the above embodiment and modes prepared by combining components in different embodiments are within the scope of the present disclosure.

For example, in the embodiment, the medical support robot 100 and the medical robots 10A and 10B communicate with each other through wired communication or wireless communication. However, the present embodiment is not limited to this. For example, the medical support robot 100 may communicate with the manipulation inputters 20A and 20B for the medical robots 10A and 10B through wired communication or wireless communication. The medical robots 10A and 10B may communicate with the manipulation inputter 30 for the medical support robot 100 through wired communication or wireless communication. The manipulation inputter 30 and the manipulation inputters 20A and 20B may communicate with each other through wired communication or wireless communication. Light, sound, or a combination of light and sound may be used as a means of communication between the medical support robot 100 and the medical robots 10A and 10B.

In the embodiment, the position of the medical support robot 100 is detected by using the position detector 109 mounted on the medical support robot 100. However, the present embodiment is not limited to this. The position of the medical support robot 100 may be detected by using a device located outside the medical support robot 100. For example, the position of the medical support robot 100 may be detected by analyzing an image of the medical support robot 100 taken by a camera from an outside of the medical support robot 100. The position of the medical support robot 100 may be detected by using a measurement value of a distance measurement sensor, such as a laser sensor, a Lidar, or an ultrasound sensor, located outside the medical support robot 100.

In the embodiment, the medical support robot 100 includes one robotic arm 102 but may include two or more robotic arms. In this case, the two or more robotic arms may include a robotic arm handling the medical instrument MD that has not yet been used for the treatment of the medical practice target person and a robotic arm handling the medical instrument MD that has already been used for the treatment of the medical practice target person. With this, the medical instrument MD that has not yet been used is prevented from being contaminated by the robotic arm and the end effector which have handled the medical instrument MD that has already been used for the treatment of the medical practice target person.

In the embodiment, the medical support robot 100 may include a structure that can close and open the storage 105. For example, the medical support robot 100 may include a door that opens and closes the storage 105. With this, the medical instrument MD that is in the storage 105 and has not been contaminated is prevented from being contaminated, and the source of contamination of the medical instrument MD that has been contaminated is prevented from diffusing.

In the embodiment, the medical support robot 100 can disinfect targets other than the medical support robot 100 by using the ejector 110*b* of the disinfector 110. However, the present embodiment is not limited to this. For example, the medical support robot 100 may disinfect the medical support robot 100 by using the ejector 110*b*.

In the embodiment, the medical support robot 100 includes the ejector 110*b* of the disinfector 110 at the robotic arm 102 or the end effector 103. However, the present embodiment is not limited to this. For example, the medical support robot 100 may include the ejectors 110*b* at the robotic arm 102 and the end effector 103. Instead of or in addition to the ejector 110*b* at the robotic arm 102 or the end effector 103, the medical support robot 100 may include another ejector 110*b* at a place other than the robotic arm 102 and the end effector 103. With this, the medical support robot 100 can disinfect the robotic arm 102 and the end effector 103 by using the ejector 110*b*.

The medical support robot 100 according to the embodiment may include a detachable protection cover. The protection cover may cover a part of the medical support robot 100 or the entire medical support robot 100. For example, the protection cover that covers a part of the medical support robot 100 may cover a portion which requires labor and time for being disinfected or is difficult to be disinfected among portions of the medical support robot 100. With this, even if contaminants are attached to the medical support robot 100, the protection cover is replaced, and this can obtain the same effect as the disinfection of the medical support robot 100. Therefore, labor for the disinfection is reduced.

The medical robot system 1 according to the embodiment may include a disinfection equipment outside a space, such as the medical treatment room MTR, where the medical support robot 100 and the medical robots 10A and 10B are located. For example, the medical robot system 1 may include a disinfection chamber that is adjacent to the medical treatment room MTR and includes the disinfection equipment. Furthermore, the medical support robot 100 may pass through the disinfection chamber and be disinfected in the disinfection chamber immediately before the medical support robot 100 enters into the medical treatment room MTR from an outside and immediately after the medical support robot 100 gets out from the medical treatment room MTR to an outside. With this, the contaminants attached to the medical support robot 100 are prevented from getting into the medical treatment room MTR and getting out from the medical treatment room MTR.

In the medical robot system 1 according to the embodiment, the medical support robot 100 conveys the medical instrument MD to the medical robots 10A and 10B. However, the present embodiment is not limited to this. For example, the medical support robot 100 may convey the medical instrument MD to medical workers, such as doctors and nurses.

The medical robot system 1 according to the embodiment may be located at any place. For example, the medical robot system 1 may be located inside buildings (such as hospitals), temporary structures (such as tents and prefabricated structures), and movable bodies or may be located in an outdoor environment. For example, the movable bodies may be medical movable bodies, such as hospital ships and railcars.

In the embodiment, the robotic arm 102 of the medical support robot 100 is a vertically articulated robotic arm. However, the present embodiment is not limited to this. For example, the robotic arm 102 may be a horizontally articulated robotic arm, a polar coordinate robotic arm, a cylindrical coordinate robotic arm, a rectangular coordinate robotic arm, or another type of robotic arm.

Examples of aspects of the technique of the present disclosure will be described below. A medical support robot according to one aspect of the present disclosure includes: a storage that houses a medical instrument; at least one robotic arm including a tip including an end effector that handles the medical instrument; a traveling structure that supports the storage and the at least one robotic arm and travels; and a controller. The controller performs control of causing the traveling structure to move to a medical robot that is a robot that performs medical practice.

According to the above aspect, the medical support robot can convey the medical instrument to the medical robot. The medical support robot can perform work of supporting the medical practice of the medical robot. For example, since the medical robot performs the treatment of the medical practice target person, the medical robot tends to be contaminated by the infectious disease source. Therefore, there is a possibility that the medical robot needs to be disinfected each time the medical robot moves to acquire the medical instrument. Or, a person who holds the medical instrument is at high risk of being contaminated by the infectious disease source when the person approaches the medical robot. The medical support robot can reduce the frequency of the movement of the medical robot and the risk of infection of the medical workers.

In the medical support robot according to the aspect of the present disclosure, the controller may perform control of causing the robotic arm and the end effector to execute at least either one of a holding operation of causing the medical robot to hold the medical instrument in the storage or a hold releasing operation of causing the medical robot to release the medical instrument held by the medical robot.

According to the above aspect, for example, even when the medical robot itself does not have a structure that holds or releases the medical instrument or a function of executing such holding or releasing, the medical support robot can cause the medical robot to hold or release the medical instrument. Moreover, it is possible to prevent a case where the medical robot contaminated by the infectious disease source contacts and contaminates the non-contaminated medical instrument in the storage.

In the medical support robot according to the aspect of the present disclosure, the controller may receive information of the specified medical robot, and the controller may perform control of executing at least either one of the holding operation or the hold releasing operation based on the information of the medical robot.

According to the above aspect, the medical support robot can autonomously perform the conveyance of the medical instrument to the specified medical robot, the holding operation for the specified medical robot, and the hold releasing operation for the specified medical robot.

In the medical support robot according to the aspect of the present disclosure, the end effector may hold a carrying structure on which a medical practice target person rests, and the controller may perform control of causing the end effector to hold the carrying structure on which the medical practice target person is resting and causing the traveling structure to move to the medical robot.

According to the above aspect, the medical robot does not have to move to the carrying structure. The risk of the diffusion of the infectious disease source due to the movement of the medical robot is reduced. A space where the relatively large medical robot moves between the carrying structures is unnecessary. Thus, the space can be efficiently utilized.

In the medical support robot according to the aspect of the present disclosure, the controller may receive information of the specified carrying structure and information of the specified medical robot, and the controller may perform control of causing the traveling structure to move to the carrying structure, causing the end effector to hold the carrying structure, and causing the traveling structure to move to the medical robot based on the information of the carrying structure and the information of the medical robot.

According to the above aspect, the medical support robot can autonomously convey the specified carrying structure to the specified medical robot.

The medical support robot according to the aspect of the present disclosure may further include a wireless communicator that communicates with a manipulation inputter of the medical support robot through wireless communication.

According to the above aspect, the medical support robot may be manipulated by a remote manipulation inputter. With this, the risk of infection of the operator of the manipulation inputter can be reduced.

The medical support robot according to the aspect of the present disclosure, may further include: a first wireless communicator that communicates with a manipulation inputter of the medical support robot through wireless communication; and a second wireless communicator that communicates with the medical robot through wireless communication.

According to the above aspect, the medical support robot may be manipulated by a remote manipulation inputter. Moreover, since the medical support robot is not connected to the medical robot through a wire, the restriction of the movement is reduced, and the medical support robot can freely move.

The medical support robot according to the aspect of the present disclosure may further include a sound outputter that outputs sounds. The controller may perform control of receiving sound signals from a manipulation inputter of the medical support robot and causing the sound outputter to output sounds corresponding to the sound signals.

According to the above aspect, the medical support robot can output to, for example, the medical practice target person the sounds corresponding to the sound signals output from the manipulation inputter. The medical support robot can realize communication with the medical practice target person, such as communication between the operator of the manipulation inputter and the medical practice target person.

The medical support robot according to the aspect of the present disclosure may further include a sound inputter that receives an input of sounds. The controller may perform control of outputting to a manipulation inputter of the medical support robot sound signals corresponding to the sounds received by the sound inputter.

According to the above aspect, the operator of the manipulation inputter can manipulate the medical support robot by using the manipulation inputter while confirming the sounds of, for example, the medical practice target person acquired by the sound inputter at a place away from the medical support robot, such as a place where the operator cannot directly and visually confirm the medical support robot.

The medical support robot according to the aspect of the present disclosure may further include a display that outputs an image. The controller may perform control of receiving image signals from a manipulation inputter of the medical support robot and causing the display to output an image corresponding to the image signals.

According to the above aspect, the medical support robot can display the image corresponding to the image signals output from the manipulation inputter for the medical practice target person or the like. The medical support robot can realize communication with the medical practice target person, such as communication between the operator of the manipulation inputter and the medical practice target person. For example, the displayed image may be an image of the operator.

The medical support robot according to the aspect of the present disclosure may further include an imager. The controller may perform control of outputting to a manipulation inputter of the medical support robot signals of an image taken by the imager.

According to the above aspect, the operator of the manipulation inputter can manipulate the medical support robot by using the manipulation inputter while visually confirming the image taken by the imager at a place away from the medical support robot, such as a place where the operator cannot directly and visually confirm the medical support robot.

The medical support robot according to the aspect of the present disclosure may further include a position detector that detects a position of the medical support robot. The controller may perform control of outputting to a manipulation inputter of the medical support robot, information of the position of the medical support robot detected by the position detector.

According to the above aspect, the operator of the manipulation inputter can manipulate, for example, the movement of the medical support robot by using the manipulation inputter while confirming the position of the medical support robot.

The medical support robot according to the aspect of the present disclosure may further include a position detector that detects a position of the medical support robot. The controller may receive information of the specified medical robot. The controller may performs control of causing the traveling structure to move to the medical robot based on the information of the medical robot and information of the position of the medical support robot detected by the position detector.

According to the above aspect, the medical support robot can autonomously move to the medical robot based on the information of the medical robot and the position of the medical support robot.

The medical support robot according to the aspect of the present disclosure may further include: a disinfectant storage that houses disinfectant; and an ejector that is located at the end effector or the robotic arm and ejects the disinfectant. The controller may perform control of causing the ejector to eject the disinfectant to the medical robot.

According to the above aspect, the medical support robot can disinfect the medical robot. For example, the medical support robot disinfects the medical robot before causing the medical robot to hold the medical instrument. With this, the medical instrument can be prevented from being contaminated by the medical robot.

In the medical support robot according to the aspect of the present disclosure, the controller may receive information of the specified medical robot, and the controller may perform control of causing the ejector to eject the disinfectant to the medical robot based on the information of the medical robot.

According to the above aspect, the medical support robot can autonomously disinfect the specified medical robot.

A medical robot system according to one aspect of the present disclosure includes: the medical support robot according to the aspect of the present disclosure; a manipulation inputter of the medical support robot; and the medical robot.

According to the above aspect, the same effects as the medical support robot according to the aspect of the present disclosure are obtained.

In the medical robot system according to the aspect of the present disclosure, the manipulation inputter of the medical support robot may be located in a space that is isolated from a space where the medical support robot and the medical robot are located.

According to the above aspect, even when a contamination source, such as the infectious disease source, exists in the space where the medical support robot and the medical robot are located, the operator of the manipulation inputter and the contamination source are prevented from contacting each other. Therefore, the contamination of the operator is prevented.

In the medical robot system according to the aspect of the present disclosure, the medical robot may be a robot based on a surgical robot or a robot based on a general purpose robot other than the surgical robot.

According to the above aspect, an existing surgical robot or a general purpose robot other than the surgical robot can be utilized as the medical robot. With this, a new robot does not have to be manufactured even when a medical robot system needs to be built. Therefore, the medical robot system can be quickly and easily built.

All the numerals, such as the ordinal numbers and the quantities, are examples used to specifically describe the technique of the present disclosure, and the present disclosure is not limited to these numerals. Furthermore, connection relations among the components are examples used to specifically describe the technique of the present disclosure, and the connection relations that realize the functions of the present disclosure are not limited to these.

The scope of the present disclosure is defined by not the description but the claims attached hereto such that the present disclosure is carried out in various ways within the scope of the essential features of the present disclosure. Therefore, the present embodiments are exemplary embodiments and are not limiting embodiments. All changes that come within the claims and the scope of the claims or equivalents in claims and the scope of the claims intend to be covered by the claims.

REFERENCE SIGNS LIST 1 medical robot system
10, 10A, 10B medical robot
30 manipulation inputter
100 medical support robot
102 robotic arm
103 end effector
104 traveling structure
105, 105A to 105D storage
106 controller
108, 108*a*, 108*b* communicator
109 position detector
110 disinfector
110*a* disinfectant storage
110*b* ejector
121 to 123 imager
131 sound inputter
141 display
151 sound outputter
MD medical instrument
MDA carrying structure

The invention claimed is:

1. A medical support robot for providing a support function to a medical robot that directly performs a medical practice on a medical practice target, the medical support robot comprising:
   a storage that houses a medical instrument;
   at least one robotic arm including a tip including an end effector that handles the medical instrument;
   a traveling structure that supports the storage and the at least one robotic arm and travels;
   circuitry that performs control comprising causing the traveling structure to move to the medical robot based on position information of the medical robot and position information of the medical support robot; and
   a wireless communicator comprising:
      a first wireless communicator that communicates with a manipulation inputter of the medical support robot through wireless communication; and
      a second wireless communicator that communicates with the medical robot through wireless communication, wherein
   the circuitry performs control comprising causing the robotic arm and the end effector to execute one of: a holding operation of causing the medical robot to hold the medical instrument in the storage; and a hold releasing operation of causing the medical robot to release the medical instrument held by the medical robot,
   the circuitry receives information of the specified medical robot,
   the circuitry performs control in an autonomous manipulation mode comprising executing one of: the holding operation; and the hold releasing operation, based on the information of the medical robot received from the second wireless communicator,
   the end effector holds a carrying structure on which a medical practice target person rests; and
   the circuitry performs control comprising causing the end effector to hold the carrying structure on which the medical practice target person is resting and causing the traveling structure to move to the medical robot.

2. The medical support robot according to claim 1, wherein:
   the circuitry receives information of the specified carrying structure and information of the specified medical robot; and
   the circuitry performs control comprising causing the traveling structure to move to the carrying structure, causing the end effector to hold the carrying structure, and causing the traveling structure to move to the medical robot based on the information of the carrying structure and the information of the medical robot.

3. The medical support robot according to claim 1, further comprising a sound outputter that outputs sounds, wherein the circuitry performs control comprising receiving sound signals from the manipulation inputter of the medical support robot and causing the sound outputter to output sounds corresponding to the sound signals.

4. The medical support robot according to claim 1, further comprising a sound inputter that receives an input of sounds, wherein the circuitry performs control comprising outputting to the manipulation inputter of the medical support robot sound signals corresponding to the sounds received by the sound inputter.

5. The medical support robot according to claim 1, further comprising a display that outputs an image, wherein the circuitry performs control comprising receiving image signals from the manipulation inputter of the medical support robot and causing the display to output an image corresponding to the image signals.

6. The medical support robot according to claim 1, further comprising an imager, wherein the circuitry performs control comprising outputting to the manipulation inputter of the medical support robot signals of an image taken by the imager.

7. The medical support robot according to claim 1, further comprising a position detector that detects a position of the medical support robot, wherein the circuitry performs control comprising outputting to the manipulation inputter of the medical support robot, information of the position of the medical support robot detected by the position detector.

8. The medical support robot according to claim 1, further comprising a position detector that detects a position of the medical support robot, wherein:

the circuitry receives information of the specified medical robot; and the circuitry performs control comprising causing the traveling structure to move to the medical robot based on the information of the medical robot and information of the position of the medical support robot detected by the position detector.

9. The medical support robot according to claim 1, further comprising:

a disinfectant storage that houses disinfectant; and an ejector that is located at the end effector or the robotic arm and ejects the disinfectant, wherein the circuitry performs control comprising causing the ejector to eject the disinfectant to the medical robot.

10. The medical support robot according to claim 9, wherein:

the circuitry receives information of the specified medical robot; and the circuitry performs control comprising causing the ejector to eject the disinfectant to the medical robot based on the information of the medical robot.

11. A medical robot system comprising:

a medical robot of a first type comprising a robot that performs a medical practice;

a medical support robot of a second type that supports the medical robot in performing the medical practice, the medical support robot comprising:

a storage that houses a medical instrument;

at least one robotic arm including a tip including an end effector that handles the medical instrument;

a traveling structure that supports the storage and the at least one robotic arm and travels;

circuitry that performs control comprising causing the traveling structure to move to the medical robot; and a wireless communicator comprising:

a first wireless communicator that communicates with a manipulation inputter of the medical support robot through wireless communication; and a second wireless communicator that communicates with the medical robot through wireless communication, wherein the circuitry performs control comprising causing the robotic arm and the end effector to execute one of: a holding operation of causing the medical robot to hold the medical instrument in the storage; and a hold releasing operation of causing the medical robot to release the medical instrument held by the medical robot, the circuitry receives information of the specified medical robot, the circuitry performs control in an autonomous manipulation mode comprising executing one of: the holding operation; and the hold releasing operation, based on the information of the medical robot received from the second wireless communicator; and the manipulation inputter of the medical support robot, the end effector holds a carrying structure on which a medical practice target person rests; and the circuitry performs control comprising causing the end effector to hold the carrying structure on which the medical practice target person is resting and causing the traveling structure to move to the medical robot.

12. The medical robot system according to claim 11, wherein the manipulation inputter of the medical support robot is located in a space that is isolated from a space where the medical support robot and the medical robot are located.

13. The medical robot system according to claim 11, wherein the medical robot is a robot based on a surgical robot or a robot based on a general purpose robot other than the surgical robot.

* * * * *